United States Patent [19]

Brown

[11] Patent Number: 5,681,299

[45] Date of Patent: Oct. 28, 1997

[54] DISPOSABLE ARTICLE

[75] Inventor: Malcolm David Brown, Mundford, Great Britain

[73] Assignee: Ecoprogress Limited, London, United Kingdom

[21] Appl. No.: 244,130

[22] PCT Filed: Oct. 26, 1992

[86] PCT No.: PCT/GB92/01959

§ 371 Date: May 18, 1994

§ 102(e) Date: May 18, 1994

[87] PCT Pub. No.: WO93/09740

PCT Pub. Date: May 27, 1993

[30] Foreign Application Priority Data

Nov. 19, 1991 [GB] United Kingdom ............... 9124527

[51] Int. Cl.$^6$ .................................................. A61F 13/15
[52] U.S. Cl. ..................... 604/364; 604/378; 604/385.1; 604/358
[58] Field of Search .................. 604/358, 385.1, 604/364, 367, 378, 365, 366, 370

[56] References Cited

U.S. PATENT DOCUMENTS

| | | | |
|---|---|---|---|
| 3,602,225 | 8/1971 | Wiellicki | 128/287 |
| 3,606,887 | 9/1971 | Roeder | 128/290 R |
| 3,616,797 | 11/1971 | Champaigne | 128/290 |
| 3,661,695 | 5/1972 | Berliner | 161/151 |
| 3,683,916 | 8/1972 | Mesek et al. | 128/287 |
| 3,683,917 | 8/1972 | Comerford | 5/335 |
| 3,707,430 | 12/1972 | Costanza et al. | 161/123 |
| 3,762,454 | 10/1973 | Wilkins, Jr. | 150/1 |
| 3,790,067 | 2/1974 | Scheier | 229/55 |
| 3,881,487 | 5/1975 | Schrading | 128/284 |
| 3,952,347 | 4/1976 | Comerford et al. | 5/335 |
| 4,186,233 | 1/1980 | Krajewski et al. | 428/213 |
| 4,261,066 | 4/1981 | Belz | 4/222 |
| 4,372,311 | 2/1983 | Potts | 128/287 |
| 4,503,098 | 3/1985 | Potts | 427/394 |
| 4,944,734 | 7/1990 | Wallach | 604/358 |
| 4,964,857 | 10/1990 | Osborn | 604/395 |
| 5,019,069 | 5/1991 | Klemp | 604/387 |
| 5,026,363 | 6/1991 | Pratt | 604/385.1 |
| 5,026,589 | 6/1991 | Schechtman | 428/138 |
| 5,053,482 | 10/1991 | Tietz | 528/272 |
| 5,280,835 | 1/1994 | Edwards et al. | 206/484 |
| 5,429,874 | 7/1995 | VanPutte | 428/522 |

FOREIGN PATENT DOCUMENTS

| | | | |
|---|---|---|---|
| 010171 | 4/1980 | European Pat. Off. | B65D 65/38 |
| 130061 | 1/1985 | European Pat. Off. | A61L 15/00 |
| 2009120 | 1/1970 | France | A41B 13/00 |
| 0653680 | 5/1951 | United Kingdom . | |
| 1271424 | 4/1972 | United Kingdom | A61F 13/16 |
| 1389891 | 4/1975 | United Kingdom | A41B 13/02 |
| 1519480 | 7/1978 | United Kingdom | A41B 13/02 |
| 2195919 | 4/1988 | United Kingdom | A61F 5/44 |
| 2243327 | 10/1991 | United Kingdom | B32B 27/36 |
| 9003156 | 4/1990 | WIPO | A61F 13/15 |
| 9004456 | 5/1990 | WIPO | B01J 20/26 |
| 9202199 | 2/1992 | WIPO | A61F 13/15 |

*Primary Examiner*—John G. Weiss
*Assistant Examiner*—Dennis Ruhl
*Attorney, Agent, or Firm*—Webb Ziesenheim Bruening Logsdon Orkin & Hanson, P.C.

[57] ABSTRACT

A disposable article, e.g a diaper, having a backing layer (5) formed of soluble material constructed so that when in contact with a relatively large volume of liquid, e.g. that produced by flushing a lavatory, the backing layer (5) dissolves and loses its integrity but when in contact with a relatively small volume of liquid, e.g. when handled with wet hands, dissolution is restricted so that the backing layer (5) maintains its integrity. The backing layer may have variable solubility across its thickness, e.g. one side of the backing layer may comprise a relatively soluble material (4), whereas the other side comprises a less soluble material (6). Alternatively, the backing layer may comprise a soluble membrane (5) having a discontinuous layer (14, 16) of relatively insoluble material applied to at least one surface thereof.

25 Claims, 6 Drawing Sheets

DISPOSABLE ARTICLE

This application is a 371 of PCT/GB92/01959, which is the PCT application of Great Britain application 9124527.4.

TECHNICAL FIELD

This invention relates to disposable articles and more particularly to disposable composite structures such as nappies (diapers), feminine hygiene products, and incontinence products.

BACKGROUND ART

The increasing demand for disposable products is producing an escalating problem of waste build Up which contaminates the natural environment.

One of the major contributors to this build up of waste is in the domain of absorbent products. It is well known that current technologies fall short in providing materials which obviate the problem.

Consideration of current structures used to produce disposable absorbent products, especially those which absorb body fluids, reveal that they represent a health risk due to the difficulties of handling and storage in the soiled state. Attempts have been made to re-cycle such products through collection and eventual processing but any system which requires mass storage prior to re-cycling will, almost by definition, increase the risk to health and is likely to be socially unacceptable.

Whilst feminine hygiene products are routinely flushed (after being torn in half along their length prior to flushing), the materials conventionally used in the manufacture of both nappies (hereinafter called diapers) and adult incontinence products, make them incompatible with the flushing process and the subsequent sewage cycle. Diapers are, for example, usually provided with a polythene backing layer which is both insoluble and does not biodegrade.

An advance in this field is described in PCT patent specification publication No WO-A-92/02199 (priority date 10 Aug. 1990, international filing date 9 Aug. 1991 and publication date 20 Feb. 1992). This describes a composite material for providing a disposable product such as a diaper having an outer, soluble layer supporting a liquid impervious barrier, exampled by a coating, which separates the soluble layer from a disintegratable and dispersible liquid absorbent layer. However, this construction suffers from the disadvantage that although it is designed to maintain its integrity during normal use, problems arise because the outer soluble layer can dissolve if it inadvertently comes into contact with liquid, e.g. if it is handled by a person having wet hands. This problem is acknowledged in the final paragraph of WO-A-92/02199 which describes an insoluble re-usable plastics outer cover (shown in FIG. 15 thereof) in which the disposable linings can be used. This cover obviously helps protect the lining, and particularly the soluble outer layer thereof, from inadvertently coming into contact with liquid.

Another approach has been to coat a backing layer formed of a water soluble material such as polyvinyl alcohol with an alkali soluble polymer, e.g. as described in WO-A-90103156 and GB-A-2195919. In such an arrangement, the alkali soluble coating protects the backing layer from dissolving if it inadvertently comes into contact with water. However, when the diaper is flushed, it is necessary to ensure that the flushing environment is sufficiently alkaline to dissolve the polymer coating. This usually requires the addition of a pH adjuster to the flushing water.

In yet another approach described in U.S. Pat. No. 4,372,311, the surface or surfaces of a disposable article made of a water soluble polymer which are to come into contact with moisture are coated with a degradable, water-insoluble polymer. When an article with the coating applied to only one surface is flushed, the water soluble polymer dissolves leaving a thin layer of degradable, water insoluble coating which is then able to degrade over a period of time. If the water soluble polymer is coated on both sides with the water-insoluble polymer, then both of the coatings have to bio-degrade before the soluble polymer is able to dissolve.

The present invention aims at providing a disposable article which can be disposed of in a manner which causes it to dissolve and/or disintegrate more readily than the prior art whilst overcoming, or at least minimising to an acceptable level, the problems associated with moisture contamination described above without the need to use pH adjusters.

It should be noted that the term 'soluble' used herein is used in its broadest sense to refer to a material which loses its integrity when subjected to a liquid, whether this be by dissolving, disintegrating or otherwise dispersing.

DISCLOSURE OF INVENTION

This invention relates to a disposable article having a backing layer comprising a membrane formed of a material which is soluble in water such that when the article is in contact with a relatively large volume of water, eg that produced by a flushing lavatory, the membrane readily dissolves to an extent that the backing layer loses its integrity, wherein the outer surface of the membrane is adapted so as to dissolve less readily than the membrane as a whole whereby, when the outer surface is in contact with a relatively small volume of water, eg when handled with wet hands, dissolution of the membrane is restricted so that the backing layer maintains its integrity.

Other features of the invention will be apparent from the following description and from the subsidiary claims of the specification.

BRIEF DESCRIPTION OF DRAWINGS

The invention will now be further described, merely by way of example, with reference to the accompanying drawings, in which:

FIG. 12 shows a perspective view of the diaper of FIG. 11 in the shape it is likely to be used in.

BEST MODE OF CARRYING OUT THE INVENTION

Figure 1:
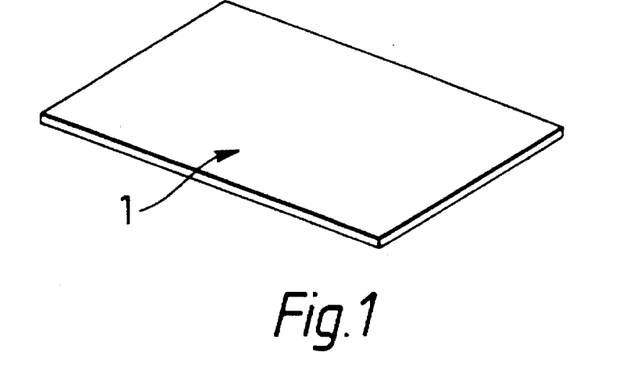
FIG. 1 shows a perspective view of a backing layer comprising just a layer of soluble material.

FIG. 1 shows a backing layer 1 comprising a single water soluble compound. Forms of this compound are exampled by polyvinyl alcohol, algenate, cellulosic derivatives, polyethylene oxide and gelatine. Such a backing layer adds mechanical strength to structures in which it is incorporated. However, this type of backing layer tends to dissolve or breakdown if it inadvertently becomes wet, e.g. if it is handled with wet hands.

In contrast to this, the composite structures described below use a backing layer formed of a soluble material constructed so that, when flushed, the backing layer dissolves and loses its integrity although it is able to maintain its integrity when it only comes into contact with a limited amount of water. One way of achieving this is by using a backing layer which has variable solubility across its thickness, e.g. a bilayer or multilayer construction which consist of different water soluble compounds or modifications of single compounds. An example of the former would be polyvinyl alcohol and hydroxy propyl cellulose, and an example of the latter would be cold and hot water soluble polyvinyl alcohol combined to form a single membrane. Other possible compounds which offer similar membrane potential are algenate, cellulosic derivatives, polyethylene oxide and gelatine. Such a construction offers advantages over membranes of single polyvinyl alcohol in that cold water only membranes are difficult to handle and hot water only membranes are not so easily flushed.

Figure 2:
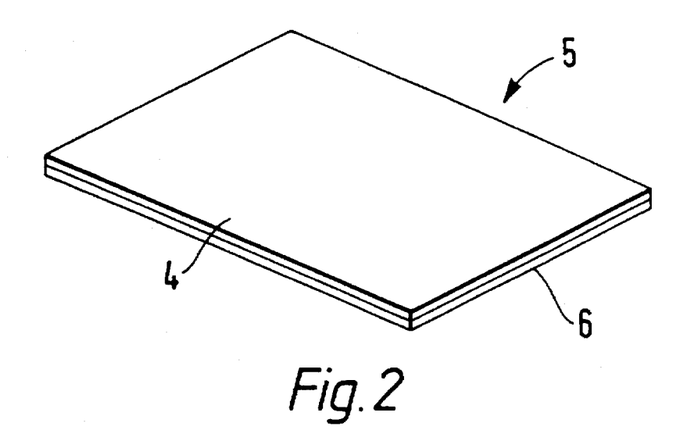
FIG. 2 shows a perspective view Of a backing layer used in a first embodiment of the invention.

FIG. 2 shows a backing layer 5 which comprises two variants of the same compound on opposite sides of the layer, for example a hot water soluble polyvinyl alcohol, indicated at 6, and a cold water soluble polyvinyl alcohol, indicated at 4.

The backing layer adds mechanical strength to a structure in which it is incorporated and when in contact with a relatively large volume of water, such as produced by the flushing action of a lavatory, the cold water soluble layer dissolves so the backing layer 5 loses its integrity. However, the hot water soluble material is sufficiently insoluble in cold water to be able to retain its integrity, although it may become a little sticky, if it comes into contact with a small volume of water, especially if this is only in localised areas as might occur, for example, if it is handled with wet hands.

Figure 3:
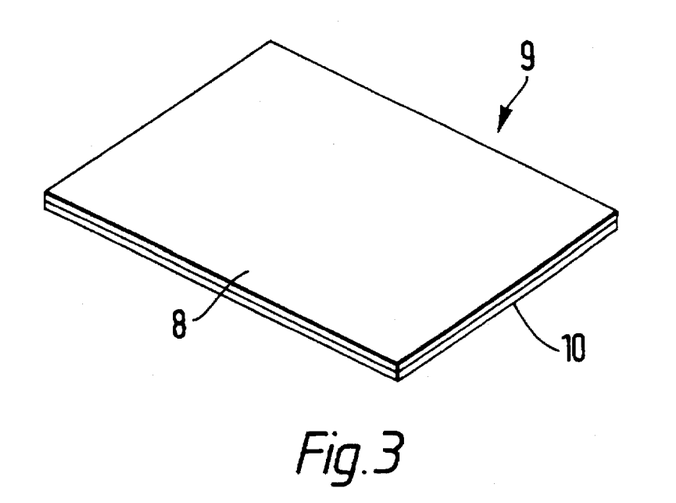
FIG. 3 shows a perspective view of a backing layer used in a second embodiment of the invention.

FIG. 3 shows another two layer backing layer 9. In this case, both layers are soluble but formed of different compounds, for example, polyvinyl alcohol 8 and hydroxypropyl cellulose 10. The layers of soluble material making up the backing layer are typically around 10 to 20 microns thick. The backing layer may, for example, comprise a 20 micron thick layer of cold water soluble material and a 10 micron thick layer of hot water soluble material. A cold water soluble layer of polyvinyl alcohol typically takes around 6 seconds to disperse in agitated water at 20 degrees Centigrade and less than 60 seconds to dissolve completely. A hot water soluble polyvinyl alcohol layer would undergo less than 15% dissolution in 90 seconds under such conditions. In contrast, a "reduced" solubility layer would typically dissolve after several hours or days and a non-soluble layer would never dissolve. It will be appreciated that solubility rates can be greatly affected by the degree of agitation, the surface area exposed to the water (which depends on folds and convolutions), by the type of polymer being used and the temperature. However, these figures provide an indication of typical solubility rates.

In another arrangement, the handling and mechanical strength of the backing membrane is improved by applying a discontinuous layer of insoluble or relatively insoluble (and preferably biodegradable) material on one or both of its sides. This has the effect of keeping the membrane intact if small areas are exposed to liquids during use. A variety of patterns can be used to achieve this effect. Conveniently, a cross hatch design is used. It will be appreciated that the term 'discontinuous' is used to describe a coating or layer which is incomplete, i.e. does not provide continuous coverage of the layer in all directions so areas of the underlying layer remain exposed.

Figure 4:
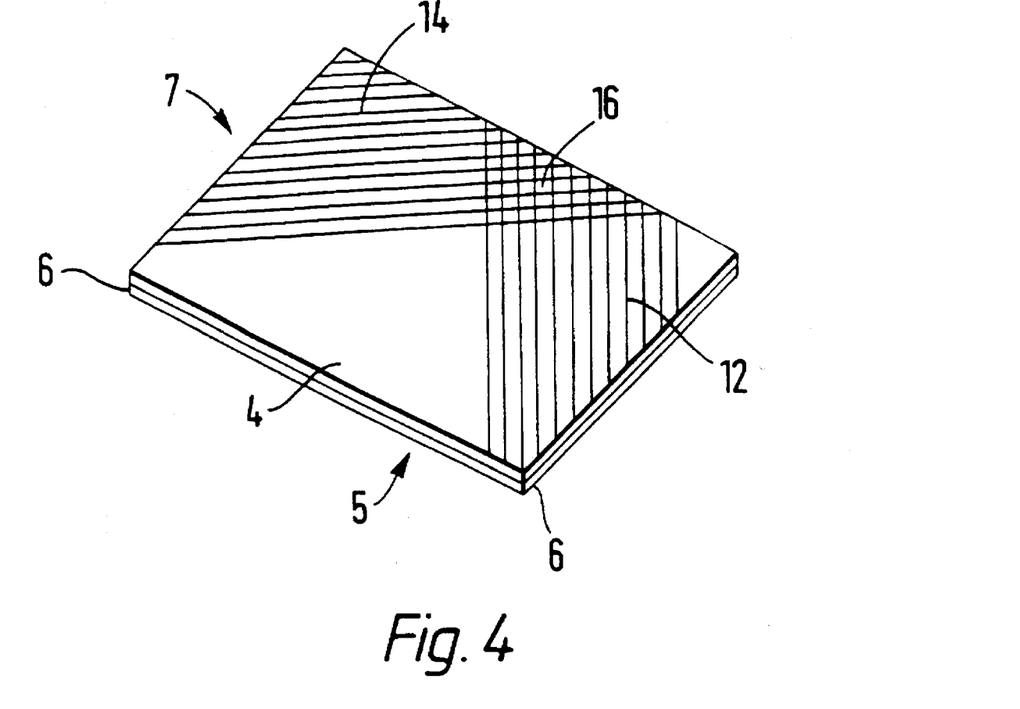
FIG. 4 shows a perspective view of a backing layer used in a third embodiment of the invention.

FIG. 4 shows, for example, a water dissolvable backing layer 7 similar to that of FIG. 2 comprising two variants of polyvinyl alcohol, indicated at 4 and 6, but with the outer surface covered by a cross hatch of non-soluble, or reduced solubility, and preferably biodegradable material shown at 12 and 14. It will be appreciated that in this example the discontinuous coating is in the form of a cross hatch as shown and covers the whole of one face of the water soluble backing layer 7. Discrete areas of water soluble membrane are thus formed by the cross-hatch pattern, as shown at 16. Other patterns such as squares, rectangles, circles, hexagons etc, in fact any pattern which can be described as discontinuous, can be used. Materials suitable for such a discontinuous pattern are preferably bio-degradable and are exampled by polycaprolactone. In use, the discontinuous pattern allows handling of the soluble membrane by containing and/or resisting any moisture contamination so any such contamination will not compromise the integrity of the soluble backing layer 7 to a point where its handling capabilities become unacceptable to the user. The discontinuous pattern allows only relatively small areas of the soluble backing layer 7 to be affected and, in the case of a cross hatch pattern, these areas are discrete. Such containment of water contamination thus reduces, if not prevents, the mechanical disintegration of the backing layer 7 as a whole in these conditions. A similar discontinuous pattern of insoluble or reduced solubility material could also be applied to a backing layer of the type illustrated in FIG. 1 which comprises just a layer of soluble material.

Figure 13:
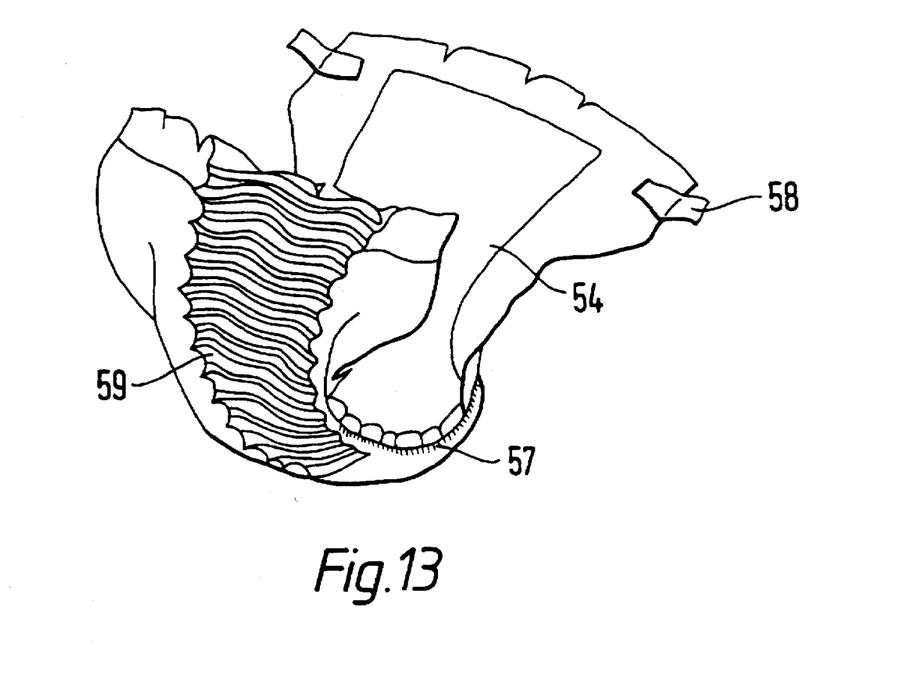
FIG. 13 shows a perspective view of another diaper.

The discontinuous coating may cover anything from around 5% to 95% of the backing layer. It need not be uniform and preferably covers a greater percentage of the surface area on those parts of the article which are most prone or vulnerable to water contamination, e.g. the central portion of a diaper. FIG. 13 illustrates a discontinuous coating in the form of relatively wide bands 59, e.g. about 9 mm wide with a spacing of around 1 mm between each band (giving about 90% coverage), which enables the diaper to withstand several exposures to wet hands without loss of integrity. Other areas of the article which are crucial to its disintegration when exposed to flushing water are provided with a lower percentage coverage of the discontinuous coating, e.g. 10% or less, or none at all.

A wide range of different types and forms of discontinuous coating may be used depending on the application. The pattern should be sufficient to offer protection against minor incidences of water contamination whilst having as little impact as possible on the break-up of the article on flushing.

An adult incontinence product is less likely, for example, to be exposed to spillages than a baby's diaper so less coverage by the discontinuous coating may be required. The pattern used may also vary. For example, a pattern which exposes only discrete areas of water soluble material may be used in the most vulnerable areas whereas a pattern which exposes lines of soluble material running across the product may be used in other areas to assist in the break-up of the product during flushing.

The other side of the backing layer (assuming the discontinuous coating is only provided on the outer surface) will dissolve only when the backing layer has become detached from the article. The dissolution of the soluble side of the layer will be reduced by the presence of the discontinuous coating on the other side, particularly if the layer becomes folded. However, most of the soluble polymer should have dissolved by the time the article reaches the sewage works.

The discontinuous layer may typically be in the range of 2 to 8 microns in thickness and is preferably formed of a biodegradable material. It can be applied by a number of coating methods including gravure and flexographic printing. The width of the lines or areas making up the coating and the size of the exposed areas therebetween will depend upon the application. The discontinuous coating will add to the strength of the backing layer as well as limiting any loss of integrity due to restricted dissolution. Resistance to dissolution may be increased by reducing the size of the exposed areas of soluble material. However, if the coating is not to cause a restriction in the break up of the product during flushing, the exposed areas should not be reduced too much. The minimum size of the exposed areas will depend on the nature and size of the product in question and the conditions during flushing but 5 mm is given as an example of the minimum width of the exposed areas.

Figure 12:
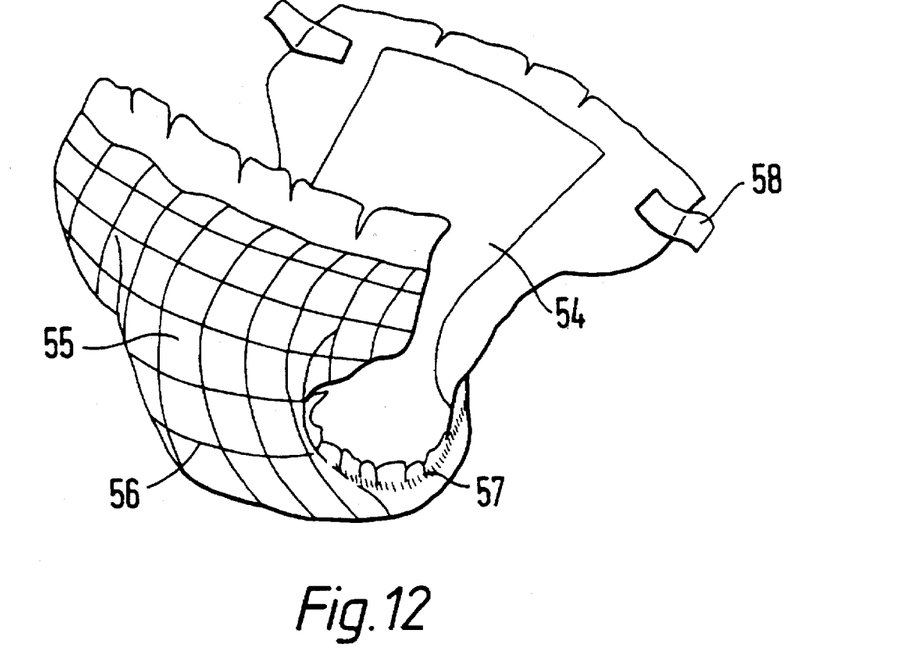

The diaper shown in FIG. 12 shows a typical example of a discontinuous coating on a 20 micron thick backing layer of cold water soluble material. In this example, the coating comprises a 3 micron thick layer of polycaprolactone and is in the form of a grid comprising 2 mm wide lines 56 enclosing 20 mm square exposed areas 55 of soluble material. Larger exposed areas may be used but at a certain point the damage caused by water contamination may, in some instances, be unacceptable. This will again depend on the nature and size of the product and the flushing conditions but 30 mm is given as an example of a maximum width for the exposed areas.

When a backing layer of the type described above is used in a composite structure, it is often desirable to provide an impervious membrane in the structure to prevent liquid absorbed by the structure from coming into contact with the backing layer (and so dissolving it). One example is a discrete liquid resistant membrane which prevents liquid absorbed by the composite structure from reaching the backing membrane. The membrane may be constructed so as to be autonomous in its own right and can be included or not depending on the use to which the final product is directed. It may comprise, for example, a 3 micron thick film of synthetic rubber. However, production and machine handling of such a thin, unsupported film is difficult and thicker films, e.g. 20 microns thick may be used to avoid these problems (although this detracts from the biodegradable nature of the article unless a biodegradable material such as Bovlon (Trade Mark) is used). This form of impervious layer has the advantage that it reduces rustling in the final product which can be important in some more discreet applications. The membrane should be flushable and is preferably constructed of bio-degradable materials.

Alternatively, the impervious membrane may comprise a thin film of impervious material supported by another layer of material. Conveniently, the membrane comprises a fibrous web coated with a water resistant resin. Such a resin can be placed on a suitable web through even dispersion and/or the application of heat. If required, resin can be placed on one side of the fibrous web and in this form the membrane thus formed will tend to curl when exposed to flushing water. This facility helps the flushing of both the membrane and the product in which it has been included.

Figure 5:
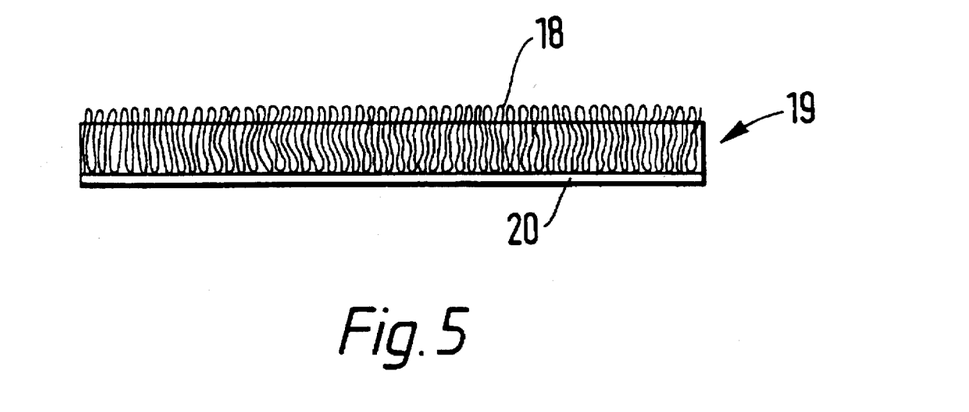
FIG. 5 shows a cross-sectional view of a substantially impervious membrane used in another embodiment of the invention.

FIG. 5 shows an impervious membrane 19 composed of fibres 18 coated on one side by a thin layer of water impervious compound indicated at 20. Both the fibres and coating are preferably bio-degradable. The fibres 18 may be in the form of a tissue (around 18 g/m$^2$) of viscose rayon, cotton or fluff pulp (a generic term for wood pulp) and the water impervious coating 20 a 3 micron coating of polycaproplactone (a bio-degradable thermoplastic polymer). The coating 20 is preferably evenly applied to the fibres 18 in the form of solution, suspension or emulsion and is heat treated to form a continuous coating on the fibres 18.

In use, the impervious coating 20 prevents liquid, classically body fluids, from reaching the fibrous element 18. When flushed, however, the fibrous element 18 becomes wet and can cause the layer 19 to curl, thus aiding mechanical disintegration of the structure in which it is included.

The layer 19 may conveniently comprise a tissue carrier of relatively low weight (e.g. 18 g/m$^2$) which gives mechanical strength, when dry, to a water impervious coating applied to one side thereof. Such a coating may be 2 to 8 microns in thickness and applied to the tissue carrier in a variety of ways. Both the tissue carrier and the impervious coating material are preferably biodegradable.

To facilitate the process of absorption and protection of the backing layer, the water impervious membrane can also be constructed in such a way that extra absorbent can be contained between two layers of bio-degradable web-like material, e.g. viscose rayon and/or cotton fibres, one layer of which has been coated with the aforementioned water resistant resin.

Figure 6:
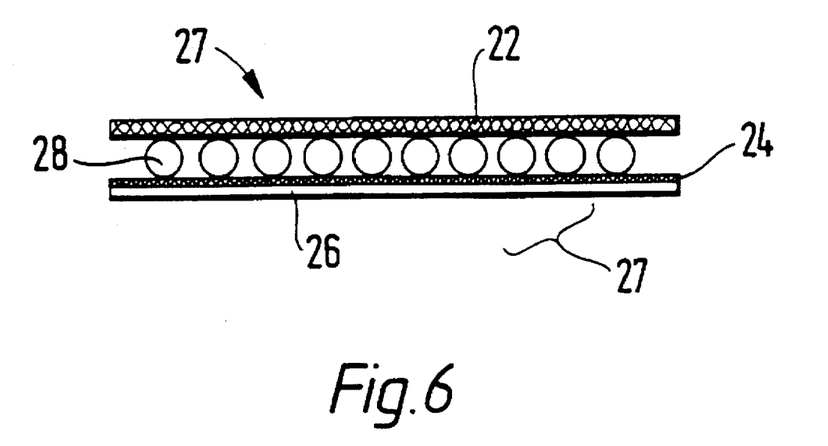
FIG. 6 shows a cross-sectional view of another version of the impervious membrane.

FIG. 6 shows an impervious layer 27 which comprises two webs 22 and 24 which enclose absorbent granules or powder, indicated at 28. One of the webs 24 has a coating of a water impervious compound 26 on one face. Liquids, classically body fluids, absorbed by the absorbent granules 28 are not transmitted through the impervious coating 26. The webs and coating are preferably of bio-degradable material. The web material is exampled by viscose rayon or cotton fibres and the impervious coating by polycaprolactone.

The impervious membrane may also be provided in the form of a water resistant coating either on the inner surface of the backing layer or on the surface of the absorbent pad facing the backing layer.

A composite structure for absorbing liquids also needs an absorbent layer or pad. The absorbent layer may be composed of fibres, absorbent fibres and absorbents used in various combinations to suit the requirement of the final product. In one example, viscose and carboxy methyl cellulose are arranged in such a manner that the layer retains sufficient integrity during use and disperses when in contact with a volume of water such as that produced by the flushing action of a lavatory. Other materials suitable for inclusion in such an absorbent layer would be algenate, modified starch, naturally occurring starch, cotton and fluff pulp. Blockage of the system is prevented through the method of construction of the absorbent layer and the particular construction design of the final product. Where the integrity of such a layer is accomplished through the use of bonding materials, exampled by polypropylene, dispersal in a volume of water is prevented, however in the described construction integrity can be provided by the fibrous material within the layer, conveniently through the addition of moisture and heat during the manufacturing process.

Figure 7:
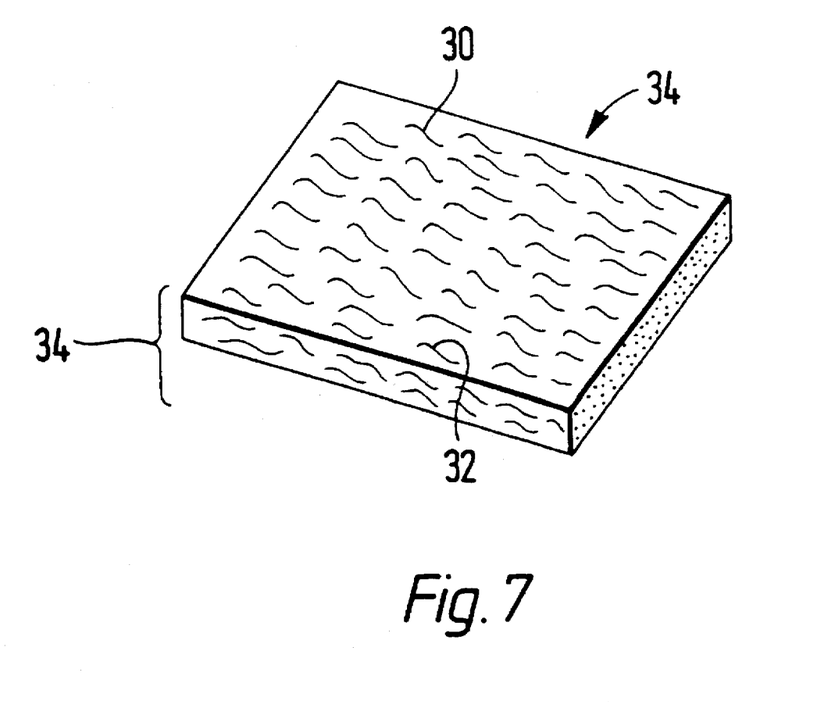
FIG. 7 shows a perspective view of an absorbent layer used in a further embodiment of the invention.

FIG. 7 shows an absorbent pad 34 containing absorbent fibres 30 together with other fibres 32. The fibres 30 may, for example, by made from acrylic based absorbent polymers and the other fibres 32 may be viscose, rayon, cotton or fluff pulp. Preferably, the fibres 30 and 32 are bio-degradable.

When in use, pad integrity can be achieved through the bonding of fibre to fibre conveniently through entanglement. The application of pressure, the addition of moisture and the input of heat during the manufacturing process are further examples of bonding techniques. Preferably, there is an absence of fibres which could be described as heat bonding fibres such as polypropylene in the described absorbent pad 34.

When liquids, classically body fluids, are absorbed by the pad 34, integrity is maintained until the pad 34 is immersed in a large volume of water, such as that available when a lavatory is flushed. When flushed, the fibres part and the pad disintegrates and the absorbent materials and the parted fibres are taken into the sewage process where they bio-degrade through the action of micro organisms.

Figure 8:
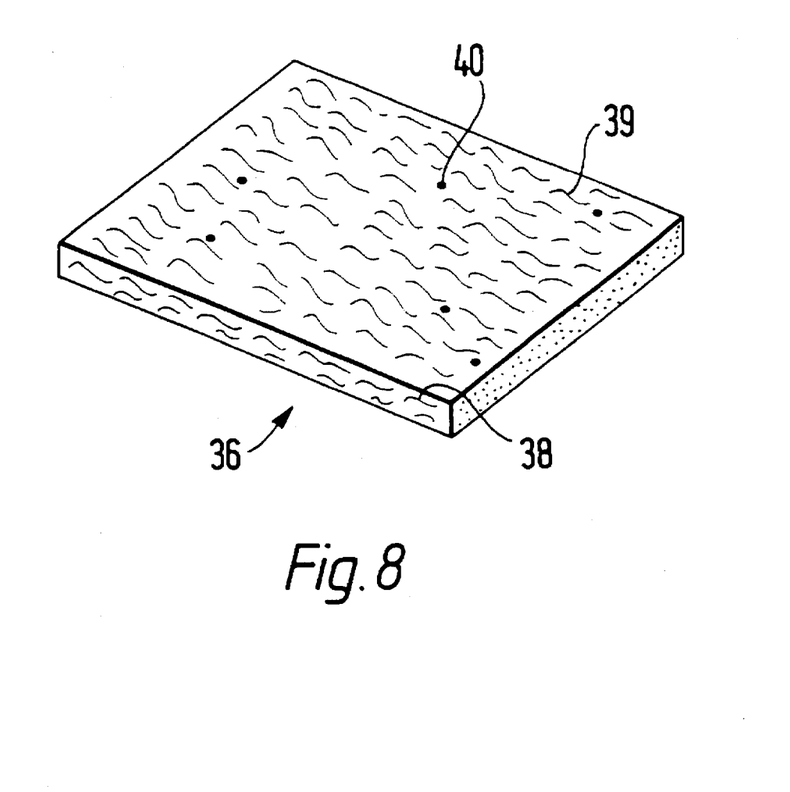
FIG. 8 shows a perspective view of another version of the absorbent layer.

FIG. 8 shows an alternative form of absorbent pad 36 which comprises absorbent fibres 38, other fibres 39 and powder or granular absorbent material indicated at 40. The absorbent material 40 is exampled by acrylic based polymers, cellulosic based compounds and natural and modified starches.

Other forms of absorbent pad (not shown) may be used, for example with fibrous material such as rayon and/or cotton. Other absorbent materials may also be contained within the pad structure and can be in any available form, for example absorbents derived from acrylic based compounds, algenate material, cellulosic material and natural and modified starches.

It is often desirable for a composite structure used to absorb liquids to be provided with a liner over the absorbent pad so the pad is not in direct contact with the user. A liner (also variously called a coverstock or scrim), if present, can be of bio-degradable materials in the form of fibres and their bonding agent. The fibres are bonded in such a manner that they have strength and integrity during use. However, during the flushing process, the liner becomes detached from the backing layer and enters the sewage cycle as a separate entity.

Figure 9:
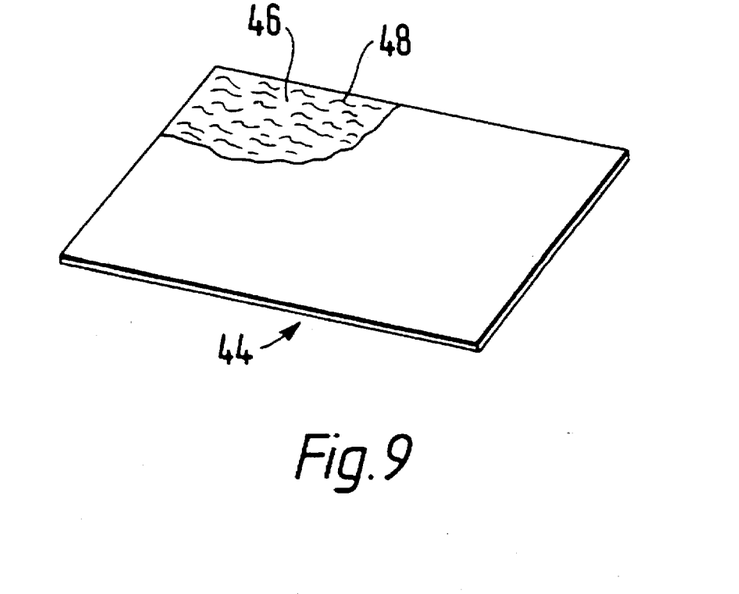
FIG. 9 shows a lining which may be used in addition to the layers described above.

FIG. 9 shows a liner 44 comprising fibres 48, e.g. viscose, rayon and/or cotton, bonded together by a heat bonding polymer 46, which is preferably bio-degradable and is exampled by the aforementioned polycaprolactone. The bonding polymer gives strength to the fibres during use but allow the passage of liquid from one side of the liner to the other.

Figure 10:
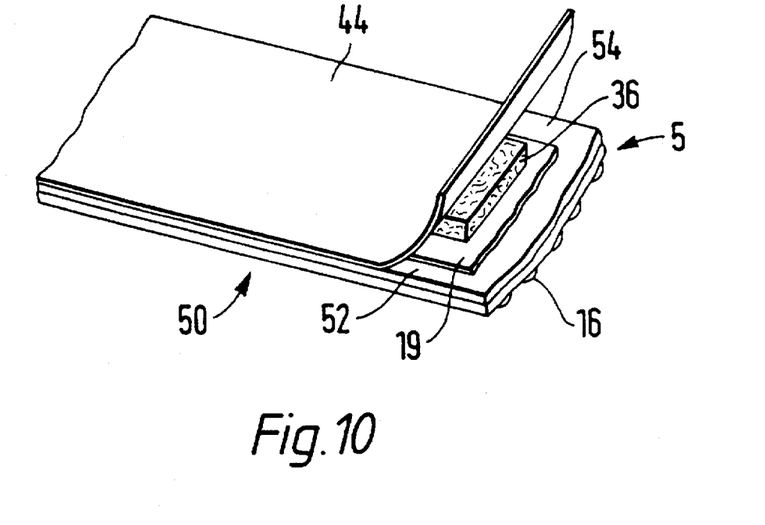
FIG. 10 shows a perspective, part broken away view of one form of a composite structure comprising a backing layer, a substantially impervious layer, an absorbent layer and a lining layer.

FIG. 10 shows a composite structure 50 formed from the various components described above. The structure 50 comprises a liner 44 shown covering an absorbent pad 36 and a water impervious layer 19. In this example the liner 44 is attached to a soluble backing layer 5, by the use of suitable adhesives (preferably water soluble and biodegradable), at edges 52 and 54.

During use, liquids, classically body fluids, are transmitted through the liner 44 to the absorbent pad 36 where they are absorbed. The impervious layer 19 prevents transmission of absorbed liquids from reaching the soluble backing layer 5 which is also provided with a discontinuous coating of insoluble, and preferably bio-degradable, material 16, which enables the structure to be handled without risk of disintegration.

When the structure 50 is disposed of in a volume of water, preferably flushed, the liner 44 detaches itself from the backing layer 5 as the latter dissolves. This action allows mechanical disintegration of the composite structure 50: the absorbent pad 36 breaks up into individual fibres and absorbent material, the backing layer 5 dissolves and the liner 44, together with the water impervious layer 19, are freed. All elements are then taken into the sewage system in the usual way where all those which are biodegradable are degraded by micro-organisms. This process is known as bio-degradation and is similar to that which occurs in a composting environment where the composite structure can also be disposed of.

The composite structure described above thus provides the functions of: containment of absorbed fluids whilst maintaining mechanical strength during use, handling capability, and flushing followed by mechanical degradation and bio-degradation of those materials so disposed. The problem of disposal is thus overcome and the used, soiled structure, is dealt with in the properly managed environment of the sewage system where it bio-degrades through the action of micro-organisms as described. Similarly, if disposal is performed by way of a composting environment then micro-organic bio-degradation follows.

Figure 11:
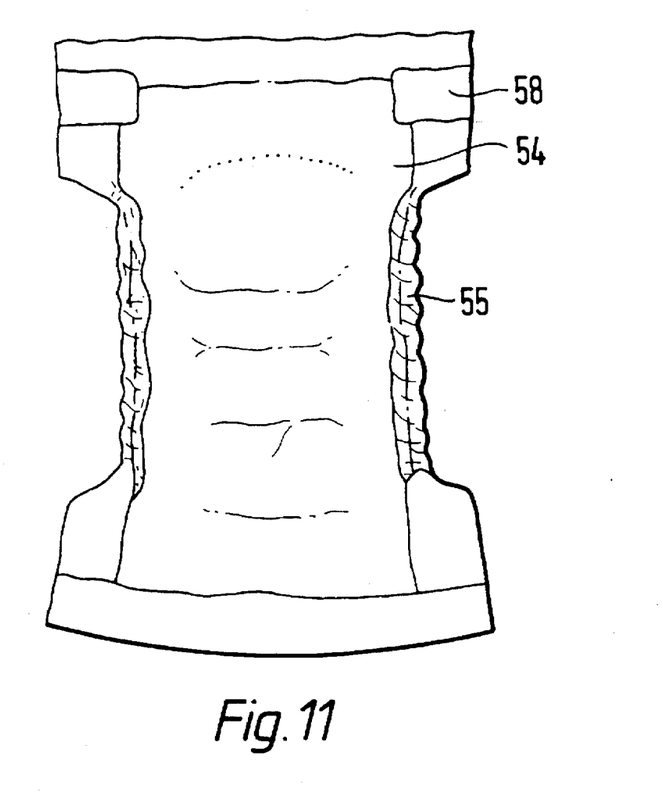
FIG. 11 shows a plan view of a composite structure in the form of a diaper when laid flat.

FIGS. 11 and 12 show a typical example of a composite structure in the form of a diaper using the various components described above. The diaper comprises a bound viscose liner 54 sealed to a water soluble backing layer 55, the exterior of which is partially coated with non-soluble material 56 to restrict its solubility. Between the backing layer 55 and liner 54 there is an absorbent pad containing a fluff pulp core boosted with a cellulose based superabsorbent and between the absorbent pad and the backing layer 55 an impervious membrane is provided comprising a barrier tissue with a thin layer of water resistant material on the side in contact with the pad. During use, this prevents the contents of the pad dissolving the backing layer 55. The backing layer 55 is in the region of 20 microns thick for reasons of expense and speed of solubility but a wide range could be used. The liner 54 is typically 18 g/m$^2$ in substance and the size of the pad will vary according to the size of the diaper. The impervious membrane is also around 18 g/m$^2$ and is coated with rubber at about 3 microns thickness. The components are put together on a nappy machine with hot melt adhesives in a conventional manner.

The discontinuous coating on the backing layer film can be achieved by several coating methods including a process similar to printing. The water resistant coating can be applied to the impervious layer in a similar manner but because it is continuous more techniques are available, including extrusion coating. The liner 54 is a bound web of viscose fibres and can be made in a number of ways including print bonding with latex or powder bonding followed by heat fusion.

The product works by virtue of the fact that in flushing water the backing layer 55 dissolves sufficiently to become detached from the liner 54 and so release the absorbant pad into the water. The impervious membrane also then becomes saturated from the back and is able to break up leaving a collapsed viscose liner 54 and a thin water resistant layer.

The absorbant pad, once released, quickly becomes a slurry which is easily dispersed. During use, the inside of the backing layer 55 is protected from dissolving by the impervious layer and the outside is protected from dissolving with wet hands etc by the areas of relatively insoluble coating 56. These areas are not sufficient, however, to prevent breaking up of the backing layer 55 in a flushing situation.

FIGS. 11 and 12 also show elastication 57, e.g. natural rubber, provided along the sides of the diaper so they fit snugly around the baby's legs and fastening means 58, such as sticky tape (e.g. a paper tape) or Velcro (trade mark) strips for holding the ends of the diaper together once it has been fitted to the baby.

FIG. 13 shows a similar diaper but with a discontinuous coating in the form of bands 59 rather than a grid pattern.

Although the backing layer has been described in relation to a composite structure in the form of a flushable disposable diaper, it is also available for other uses which would benefit from the functions it exhibits which were hitherto unavailable, for example feminine hygiene products and incontinence products. Other disposable articles which may include a backing layer of the type described above include: bedliners, bandages, bags for body waste products, toilet seat covers, etc. Such articles all include a backing layer. However, an absorbent layer and an impervious membrane etc are only required in some applications.

Such a diaper can be made entirely from bio-degradable materials with the corollary that certain components may be formed of non-biodegradable material for reasons of performance.

INDUSTRIAL APPLICABILITY

The disposable articles described above may be manufactured and used in a wide variety of applications as mentioned above.

I claim:

1. An article which is disposable in water, the article comprising: an inner side which is adapted to contain body fluid; and an outer side, the outer side comprising a backing layer which provides the article with mechanical strength, the backing layer comprising a membrane having an inner surface and an outer surface and formed of a material which is substantially entirely soluble in water such that when the article is in contact with a relatively large volume of water, the membrane readily dissolves to an extent that the backing layer loses its integrity and mechanical strength, wherein the outer surface of the membrane on the outer side of the article is soluble in water and is adapted to dissolve less readily than the inner surface of the membrane whereby, when the outer side of the article is in contact with a relatively small volume of water, dissolution of the membrane is restricted so that the backing layer maintains its integrity and mechanical strength.

2. An article as claimed in claim 1 in which the membrane has variable solubility across its thickness.

3. An article as claimed in claim 2 in which the membrane comprises two layers, an inner layer formed of a first material which is soluble in water and an outer layer formed of a second material which is less soluble in water than the first material.

4. An article as claimed in claim 2 in which the membrane has a discontinuous layer of insoluble material or of a material which is relatively insoluble compared to the material of the membrane applied to at least the outer surface thereof which restricts dissolution of the membrane.

5. An article as claimed in claim 4 in which the discontinuous layer is applied to a portion of the outer surface in a pattern which exposes only discrete areas of the membrane.

6. An article as claimed in claim 4 in which the discontinuous layer covers between 5% and 95% of the outer surface.

7. An article as claimed in claim 6 in which the discontinuous layer is applied in a pattern which leaves areas of the membrane exposed, said areas having a width of between 2 mm and 30 mm.

8. An article as claimed in claim 1 in which the membrane has a discontinuous layer of insoluble material or of a material which is relatively insoluble compared to the material of the membrane applied to at least the outer surface thereof which restricts dissolution of the membrane.

9. An article as claimed in claim 8 in which the discontinuous layer is applied to a portion of the outer surface in a pattern which exposes only discrete areas of the membrane.

10. An article as claimed in claim 8 in which the discontinuous layer covers between 5% and 95% of the outer surface.

11. An article as claimed in claim 10 in which the discontinuous layer is applied in a pattern which leaves areas of the membrane exposed, said areas having a width of between 2 mm and 30 mm.

12. An article as claimed in claim 1 comprising an absorbent layer and a further membrane substantially impervious to water interposed between the absorbent layer and the backing layer.

13. An article as claimed in claim 12 in which the further membrane comprises a fibrous web having a layer of water resistant material applied to at least one surface thereof.

14. An article as claimed in claim 12 in which the further membrane comprises a film of water impervious material.

15. An article as claimed in claim 12 in the form of a diaper.

16. An article as claimed in claim 12 comprising a liner covering the absorbent layer on a side opposite to the backing layer to prevent the absorbent layer from coming into direct contact with a user.

17. An article as claimed in claim 16 wherein an outer edge portion of the backing layer and an outer edge portion of the liner extend beyond outer edges of the absorbent layer and the water-impervious membrane, and wherein the outer edge portion of the liner is attached to the outer edge portion of the backing layer so that when the article is in contact with a relatively large volume of water the water-soluble membrane of the backing layer dissolves, causing the backing layer to lose its integrity, whereby the outer edge portion of the liner becomes detached from the outer edge portion of the backing layer thus releasing the absorbent layer and the water-impervious membrane.

18. An article which is disposable in water, the article comprising a backing layer which includes a membrane having an inner surface and an outer surface and formed of a material which is soluble in water such that when the article is in contact with a relatively large volume of water, the membrane readily dissolves to an extent that the backing layer loses its integrity, wherein an outer surface of the membrane is adapted to dissolve less readily than the inner surface whereby, when the outer surface of the article is in contact with a relatively small volume of water, dissolution of the membrane is restricted so that the backing layer maintains its integrity, wherein the membrane has a discontinuous layer of insoluble material or of a material which is relatively insoluble compared to the material of the membrane applied to at least the outer surface thereof which restricts dissolution of the membrane.

19. An article as claimed in claim 18 in which the discontinuous layer is applied to a portion of the outer surface in a pattern which exposes only discrete areas of the membrane.

20. An article as claimed in claim 18 in which the discontinuous layer covers between 5% and 95% of the outer surface.

21. An article as claimed in claim 20 in which the discontinuous layer is applied in a pattern which leaves areas of the membrane exposed, said areas having a width of between 2 mm and 30 mm.

22. An article as claimed in claim 18 wherein the membrane has variable solubility across its thickness, the outer surface being less soluble in water than an inner surface thereof.

23. An article as claimed in claim 22 in which the discontinuous layer is applied to a portion of the outer surface in a pattern which exposes only discrete areas of the membrane.

24. An article as claimed in claim 22 in which the discontinuous layer covers between 5% and 95% of the outer surface.

25. An article as claimed in claim 24 in which the discontinuous layer is applied in a pattern which leaves areas of the membrane exposed, said areas having a width of between 2 mm and 30 mm.

* * * * *